(12) United States Patent
Müller et al.

(10) Patent No.: US 7,223,808 B2
(45) Date of Patent: *May 29, 2007

(54) TEMPORARY ADHESIVE FOR METAL-METAL AND METAL-CERAMIC BONDS

(75) Inventors: Wolf-Dieter Müller, Berlin (DE); Georg Berger, Zepernick (DE); Emil Nagel, Bad Säckingen (DE); Klaus-Peter Lange, Berlin (DE)

(73) Assignees: Humboldt Universitaet Berlin Carite Universitaetsklinikum (CCM) (DE); Bam Bundesanstalt Fuer Materialforschung und -Pruefung (DE); Vita Zahnfabrik H. Rauter GmbH & Co. KG (DE)

( * ) Notice: Subject to any disclaimer, the term of this patent is extended or adjusted under 35 U.S.C. 154(b) by 581 days.

This patent is subject to a terminal disclaimer.

(21) Appl. No.: 10/480,917

(22) PCT Filed: Jun. 14, 2002

(86) PCT No.: PCT/DE02/02227

§ 371 (c)(1),
(2), (4) Date: Dec. 15, 2003

(87) PCT Pub. No.: WO02/102426

PCT Pub. Date: Dec. 27, 2002

(65) Prior Publication Data

US 2004/0175409 A1    Sep. 9, 2004

(30) Foreign Application Priority Data

Jun. 15, 2001   (DE) ............................... 101 29 845

(51) Int. Cl.
*C08K 3/32* (2006.01)
*A61K 6/00* (2006.01)
*A61F 2/28* (2006.01)
*C03C 3/247* (2006.01)

(52) U.S. Cl. ............. 524/414; 523/113; 523/118; 501/44; 623/23.62

(58) Field of Classification Search ........... 523/113, 523/118; 623/23.62; 501/44; 524/414
See application file for complete search history.

(56) References Cited

U.S. PATENT DOCUMENTS

| 5,641,347 A | * | 6/1997 | Grabowski et al. ............ 106/35 |
| 6,160,033 A | | 12/2000 | Nies |
| 6,767,854 B2 | * | 7/2004 | Berger et al. .................. 501/10 |
| 2004/0138759 A1 | * | 7/2004 | Muller et al. ............. 623/23.62 |

FOREIGN PATENT DOCUMENTS

| DE | 25 18 153 C2 | | 10/1976 |
| DE | 248351 B5 | * | 2/1995 |
| DE | 196 41 775 A1 | | 2/1998 |
| DE | 196 35 205 A1 | | 3/1998 |
| DE | 197 44 809 C1 | | 7/1999 |
| GB | 1 091 476 | | 11/1967 |

* cited by examiner

*Primary Examiner*—Tae H Yoon
(74) *Attorney, Agent, or Firm*—Akerman Senterfitt

(57) ABSTRACT

The invention relates to a method for the production of an adhesive and an adhesive kit for joining similar or different metal surfaces or ceramics, especially in the field of biomedicine. The objective of the invention is to avoid polymerization-linked by-products and disadvantageous effects, in addition to enabling a temporary biocompatible bond between metal and metal or metal and ceramics. The inventive method consist in using a monomer-free polymethylmethacrylate which is mixed with a suitable, non-toxic solvent and a bioactive vitreous-crystalline material with a particle size ranging from 0.05–20μ, consisting of 15–45 wt. % CaO, 40–45 wt. % $P_2O_5$, 10–40 wt. % $ZrO_2$ and 0.7–3.5 wt. % fluoride, having apatite and calcium zircon phosphate as main crystal phases and a glass phase as an auxiliary component until a flowable mixture is obtained. The invention also relates to an adhesive kit consisting of said components. Sufficient amounts of resistance are obtained for a temporary bond, enabling the bond to be neutralized when desired.

20 Claims, No Drawings

TEMPORARY ADHESIVE FOR METAL-METAL AND METAL-CERAMIC BONDS

CROSS REFERENCE TO RELATED APPLICATION

This application is a national stage of PCT/DE02/02227 filed Jun. 14, 2002, and based upon DE 101 29 845.5 filed Jun. 15, 2001 under the International Convention.

FIELD OF THE INVENTION

The present invention relates to a method for the production of an adhesive and an adhesive kit for joining similar or different metal surfaces or ceramics, especially in the field of biomedicine.

BACKGROUND OF THE INVENTION

Known bone cements for anchoring joints and repairing other bone defects consist of a synthetic material which as a rule is based on methylmethacrylate or related substances, in some cases with the addition of further esters of acrylic acid or methacrylic acid. Such bone cements are described e.g. in DE 196 41 775 A1. Frequently, a combination of benzoyl peroxide and dimethyl-p-toluidine is used as a catalyst in the liquid monomer, which is pointed out as a disadvantage in DE 196 35 205. Bone cements are usually prepared by mixing two components. One component contains the liquid monomer, the other is made up of a powdery polymer provided in the form of spherical particles having a diameter of approx. 100 μm.

Such bone cements or other adhesives used e.g. in dentistry are intended to endure for a very long time and usually do not allow the adhesive bond to be undone earlier, e.g. for inspection.

Another general problem with regard to materials to be polymerized consists in that heat is exothermally released during the polymerization. However, the bone cells which are in contact with said materials are damaged if the temperature rises above 50° C. The actual thermal stress put on body cells within the zone of contact with the polymerizing bone cement can only be predicted very inaccurately. It depends on the thickness of the cement layer applied, the thermal conductivity via the prosthesis components as well as the bone itself. Laboratory tests have shown that maximum temperatures up to 110° C. may be reached during the polymerization of commercially available cements under certain conditions, causing burns as a consequence. Improvements seem to be necessary in this respect.

Another problem of the bone cements known so far is due to the fact that residual monomer inevitably contained therein as well as other additives, e.g. the stabilizer hydroquinone (toxicity class 3) and the accelerator N,N-dimethyl-p-toluidine (toxicity class 2), may dissolve out, thus causing damage.

SUMMARY OF THE INVENTION

The object of the invention is to avoid current polymerization-linked components or effects with regard to adhesive bonds in the field of biomedicine, in addition to enabling a temporary biocompatible bond between metal and metal or metal and ceramics.

The inventive method for the production of a temporary adhesive solves the aforesaid problems by avoiding polymerization itself during the synthesis of the adhesive and by adding a special bioactive material. According to the invention, said method consists in that 15 to 50% by weight of a monomer-free polymethylmethacrylate (PMMA) whose average molar mass ranges between 3,000 and 200,000 daltons and whose acid value ranges between 10 and 350 mg KOH per g polymer is mixed with a biocompatible, organic solvent or solvent mixture for the PMMA and 0.05 to 80% by weight of a bioactive, vitreous-crystalline material with a particle size ranging between 0.05 and 20 μm is added to the mixture while stirring and at a temperature ranging between 10 and 50° C. until a flowable mixture is obtained whose open processing time ranges between 1 and 20 minutes, wherein the vitreous-crystalline material consists of 15–45% by weight CaO, 40–45% by weight $P_2O_5$, 10–40% by weight $ZrO_2$ and 0.7–3.5% by weight fluoride and contains apatite and calcium zirconium phosphate as main crystal phases and a glass phase as an auxiliary component, said main crystal phases jointly making up at least 35% by weight and said auxiliary components making up 5 to 15% by weight.

Further, 3 to 30% by weight of a biocompatible powder containing zinc and/or a totally or partially resorbable bioceramic material may be added to the mixture.

The mixture can be introduced in the body and set therein at body temperature since no polymerization reaction takes place within said mixture. For this purpose, a PMMA whose acid value has been modified and having a molar mass as indicated above is dissolved in a suitable solvent, e.g. ethyl acetoacetate or mixtures of ethyl acetoacetate with ethanol, which ethanol may contain water up to an amount of 4% by volume. The sticky, flowable component obtained in this way is mixed with a powder mixture of the vitreous-crystalline material and optionally e.g. ZnO and totally or partially resorbable and/or long-term stable bioceramic and optionally $TiO_2$. The particle size of all powdery components ranges between 0.005 and 20 μm. As a result of the aforesaid procedure, a flowable, sprayable and spreadable mass is obtained ex vivo, which can be processed during a period of several minutes, e.g. 1–10 min, depending on the amount of powder contained therein.

DETAILED DESCRIPTION

It is preferred that a polymethylmethacrylate be used in an amount ranging between 30 and 35% by weight.

The average molar mass of the PMMA may preferably range between 20,000 and 80,000 daltons.

The acid value may preferably range between 25 and 65 mg KOH per g polymer. In this context, the acid value indicates the amount of KOH in mg required to neutralize 1 g of the polymer sample. It is an essential criterion as the number of free carboxyl groups of the polymer is important with regard to bonding to the metal components.

The acrylate whose acid value has been modified can be produced from methylmethacrylate and methacrylic acid by means of a suspension polymerization, wherein the ratio of the molar masses has to be selected such that the desired acid value is achieved. Alternatively, the polymer whose acid value has been modified can be obtained by alkaline saponification of a polymer consisting of methylmethacrylate and ethylmethacrylate. The ethylmethacrylate makes up 2 to 10 moles, preferably 6 moles.

A preferred vitreous-crystalline material contains 23–39% by weight CaO, 40–45% by weight $P_2O_5$, 20–35% by weight $ZrO_2$ and 1–6% by weight fluoride and contains apatite and calcium zirconium phosphate as main crystal phases and a glass phase as an auxiliary component, said main crystal phases jointly making up at least 35% by weight and said auxiliary components making up 5 to 15% by weight.

Another preferred vitreous-crystalline material contains 23–39% by weight CaO, 40–45% by weight $P_2O_5$, 20–35% by weight $ZrO_2$ and 1–3% by weight fluoride and in addition 0.1–6% by weight $Na_2O$ and contains apatite and calcium zirconium phosphate as main crystal phases and a glass phase as an auxiliary component and a sodium zirconium phosphate phase as an additional auxiliary component. Said main crystal phases jointly make up at least 35% by weight and each of said auxiliary components can make up 5 to 15% by weight.

In addition, the vitreous-crystalline material according to the invention may contain 0.1 to 6% by weight magnesium oxide and/or potassium oxide and the corresponding additional phases.

The amount of $Na_2O$, MgO and/or $K_2O$ contained preferably ranges between 1 and 6% by weight. The corresponding secondary crystal phase, i.e. sodium zirconium phosphate, preferably makes up 5 to 10% by weight.

The vitreous-crystalline material is produced by preparing a mixture of suitable substances, i.e. 15–45% by weight CaO, 40–45% by weight $P_2O_5$, 10–40% by weight $ZrO_2$ and 0.7–3.5% by weight fluoride. Advantageously, the fluoride is added in the form of $CaF_2$. The aforesaid components are combined with one another, subjected to suitable, mostly multi-stage thermal treatment programs (holding stages in the range between 400 and 1,500° C.) and finally melted at between 1,550 and 1,650° C. in a suitable crucible material, preferably consisting of a Pt/Rh alloy. The melt is poured and once it has solidified the mass is cooled down to room temperature in air (spontaneous cooling) or in a cooling furnace, depending on its intended use. Finally, the material is ground.

In general, the terms "glass ceramic" and "vitreous-crystalline material" used herein cannot always be clearly defined. Both crystalline and vitreous and/or X-ray amorphous phases are provided in a thoroughly mixed state. It is of no importance for the present invention whether one phase is located adjacent to the other or one phase encloses the other.

The term "main crystal phase" as used herein refers to a crystalline phase which is contained in at least twice the amount of a secondary phase, concentrations of approx. 15% and below, preferably below 10% by weight, being referred to as secondary phases.

The particle size is measured by means of laser granulometry.

The bioceramic material which may be used in addition to said vitreous-crystalline material is preferably selected from among materials containing sodium, potassium, calcium, magnesium hydroxyl ions or hydroxyl components, fluoride, silicate and/or orthophosphate. A preferred bioceramic material contains crystalline phases of $Ca_2KNa(PO_4)_2$. By adding resorbable bioceramics, porous structures can be achieved which may have osteoconductive effects and at the same time act as a support. The gradual dissolution of the bioceramic particles depends on the structure thereof an can be adjusted as desired. Advantageous materials include e.g. a material produced according to DE 19744809 C1 or materials containing $Ca_2KNa(PO_4)_2$ or similar phases. If long-term stable, bioactive ceramics or glass ceramics are used instead, one of the crystalline phases should be apatite. An advantageous glass ceramic is based on apatite/wollastonite according to DD 247574A3.

In order to obtain a material with higher X-ray density, it is recommended that a material be admixed to the adhesive according to the invention which consists of the following components or contains the same in amounts above 30% by weight: $CaZr_4(PO_4)_6$ and/or $CaTi_4(PO_4)_6$. It is of no importance for the intended use of the adhesive whether calcium zirconium phosphate and/or calcium titanium orthophosphate is provided in an amorphous or rather in the more typical crystalline form.

Further, it may be advantageous that $TiO_2$ be added as an additional inorganic filler, preferably in an amount ranging between 0.1 and 10% by weight and preferably in the form of its modification rutile, thereby achieving considerably higher strengths.

The biocompatible powder containing zinc used may be zinc oxide or a zinc soap. Zinc soaps, which belong to the group of metallic soaps, are salts containing the rests of long-chain fatty acids, oleoresin acids and naphthenic acids such as stearates, palmitates, oleates, linoleates, resinates, laurates, octanoates, ricinoleates, 12-hydroxystearates, naphthenates, tallates, etc.

The setting reaction can also be controlled via the formation of zinc soaps and the supply of water from the surrounding tissue. There is no need to add water.

Due to its structure, the adhesive has a certain stickiness with respect to metal oxides and, as a result, adheres better to the outer oxide layer of e.g. ceramic surfaces or implants made of titanium alloys.

The inventive method may include the incorporation of medicines, e.g. antibiotics, which advantageously may be added to individual components of the mixture, e.g. the vitreous-crystalline or the bioceramic material, or added into the mixture as a separate component. Preferably, gentamicin is added in an amount ranging between approx. 0.5 and 2% by weight, preferably 0.8 and 1.3% by weight, relative to the total weight of the adhesive.

A particular advantage of the adhesive according to the invention consists in that it is a monomer-free adhesive which is easy to mix, whose thixotropy and/or pore size is adjustable and which does not release any toxic substances into the surrounding tissue. In particular, the adhesive has absolutely no toxic effect since monomers as well as the usual stabilizers and accelerators are avoided. Another advantage consists in that the adhesive does not set during the mixing process, i.e. in 1 to 10 minutes, preferably 4–5 min, but remains plastic during 3 to 8 min on average.

All the aforesaid features enable the adhesive to be evenly spread on a metal or ceramic surface, resulting in a uniform thickness of the adhesive layer applied thereto. In this way, a uniform contact between the surfaces to be joined to one another by the adhesive can be ensured. Processing errors occur much more seldom.

The setting process is brought about by the formation of chelates. Said chelates may be formed by a reaction with the $Zn^{2+}$ ions added, but in part also with the soluble components of the two ceramics as well as components contained in the surface of the materials to be joined.

The temporary adhesive according to the invention enables a bond between metal and metal, which metals can be the same or different, and metal and ceramics to be established for a certain period of time, which may be particularly desirable in dentistry, e.g. when fixing metallic implants to ceramic crowns or metallic implants to gold crowns. In many cases, it is advantageous to undo such joints after several weeks or months or even up to 2 years in order that the dentist may evaluate certain effects on the tissue surrounding the implant or remove deposits in the area around and below the crown. Adhesive bonds established by means of known bone cements or adhesives usually cannot be undone in a targeted manner, i.e. without damaging any or several of the crown, the implant or the surrounding gum.

The strengths of the adhesive according to the invention are such that the patient's use of their dentures is in no way restricted.

The invention further relates to an adhesive kit based on polymethylmethacrylate characterized by the following components provided separate of one another:
a) 15 to 50% by weight of a monomer-free polymethylmethacrylate (PMMA) whose average molar mass ranges between 3,000 and 200,000 daltons and whose acid value ranges between 10 and 350 mg KOH per g polymer;
b) 5 to 40% by weight of a biocompatible organic solvent or solvent mixture for the PMMA;
c) 0.05 to 80% by weight of a vitreous-crystalline material with a particle size ranging between 0.05 and 20 µm consisting of 15–45% by weight CaO, 40–45% by weight $P_2O_5$, 10–40% by weight $ZrO_2$ and 0.7–3.5% by weight fluoride and containing apatite and calcium zirconium phosphate as main crystal phases and a glass phase as an auxiliary component, said main crystal phases jointly making up at least 35% by weight and said auxiliary components making up 5 to 15% by weight.

Said kit may further contain 3 to 30% by weight, relative to the total weight of the kit, of a biocompatible powder containing zinc and/or a resorbable bioceramic material according to DE 197 44 809 or EP 0541546 and/or a long-term stable bioceramic material according to DD 247 574.

In addition, the bone cement kit may contain amounts of $TiO_2$, either mixed with component c) or provided separately, as well as an X-ray contrast medium, either mixed with component c) or provided separately, preferably up to 30% by weight $CaZr_4(PO_4)_6$ or $CaTi_4(PO_4)_6$ or mixtures thereof.

The biocompatible solvent included in the adhesive kit according to the invention is ethyl acetoacetate or a mixture of ethyl acetoacetate with ethanol, which ethanol may contain water up to an amount of 4% by volume.

It is advantageous that the biocompatible powder containing zinc be zinc oxide or a zinc soap.

The kit according to the invention is sterilized using ethylene oxide or by means of radiation and provided in a sterilized form.

The kit may further contain medicinal components, which are either mixed with the individual components or provided separately, particularly antibiotics.

The invention will hereinafter be explained in more detail by means of examples. All percentages are by weight.

EXAMPLE 1

Production of the Vitreous-Crystalline Material Apatite/CZP1

A mixture having the following composition is prepared (Code: Apatite/CZP1):
25.88 CaO
28.44 $ZrO_2$
43.68 $P_2O_5$
5.00 $CaF_2$.

In doing so, the amount of CaO can be added in the form of 62.79 $CaHPO_4$ and the required amount of $P_2O_5$ can be incorporated in the form of 10.51 ml of an 85% $H_3PO_4$.

First, $CaHPO_4$, $ZrO_2$ and $CaF_2$ are thoroughly mixed, then the phosphoric acid is added, the mixture is left to react and subsequently ground in a mortar, the process including holding stages at 120° C. and 170° C. lasting 4 hours each and intended to dry the product. The reaction mixture obtained in this way is filled into a Pt/Rh crucible, heated up to 400° C., held at this temperature for 1 hour, heated up to 800° C., held at this temperature for 1 hour, cooled and ground in a mortar. The material pretreated in this way is now melted in a Pt/Rh crucible, the melting process including holding times of 15 min at 800, 1,000, 1,300, 1,500 and finally 1,600° C. respectively, and poured onto a steel plate (room temperature).

Once the melt has solidified, part of the material obtained is milled in an agate mill and particles below 43 µm are separated by sieving and analyzed by means of X-ray diffractography. The result (X-ray diffractogram) shows that the crystal phases apatite (fluoroapatite/hydroxyapatite) and calcium zirconium phosphate [$CaZr_4(PO_4)_6$] are clearly detectable in the vitreous-crystalline product. The remaining part of the solidified melt is comminuted until a particle size of 0.05–20 µm is achieved.

EXAMPLE 2

Production of the Vitreous-Crystalline Material Apatite/CZP2

A mixture is prepared according to the instructions of Example 1, except that sodium oxide is added as an additional component (Code: Apatite/CZP2). Specifically, the following components are mixed:
59.93 $CaHPO_4$
27.10 $ZrO_2$
3.42 $Na_2O$
5.00 $CaF_2$ and
9.56 ml of an 85% $H_3PO_4$.

Processing is done as in Example 1. At the end of the last temperature holding stage, the melt is poured out of the crucible onto a steel plate.

Once the melt has solidified, part of the material obtained is milled in an agate mill and particles below 43 µm are separated by sieving and analyzed by means of X-ray diffractography. The result (X-ray diffractogram) shows that the crystal phases apatite (fluoroapatite/hydroxyapatite) and calcium zirconium phosphate [$CaZr_4(PO_4)_6$] and sodium zirconium phosphate [$NaZr_2(PO_4)_3$] are detectable in the vitreous-crystalline product.

The remaining part of the solidified melt is comminuted until a particle size of 0.05–20 µm is achieved.

EXAMPLE 3

Coefficients of Expansion of Apatite/CZP1

A vitreous-crystalline material according to Example 1 was produced (Apatite/CZP1). The material was milled in a mill lined with zirconium oxide until a $D_{50}$-value of 8 µm was achieved. The ground material was combined with a 5% polyvinylalcohol (PVA) solution, the ratio of ground material to PVA solution being 90 to 10% by weight, and the mixture was compression-moulded into a rod applying a force of 4.7 kN. The resulting compact was sintered at a temperature of 1,050°.

Then, the thermal coefficient of expansion (CE) of the relatively dense moulded body obtained in this way was determined:

| | |
|---|---|
| CE in the range of 27–400° C.: | $1.90 * 10^{-6}$ degrees Celsius$^{-1}$ |
| CE in the range of 50–400° C.: | $1.86 * 10^{-6}$ degree Celsius$^{-1}$ |
| CE in the range of 30–300° C.: | $1.45 * 10^{-6}$ degree Celsius$^{-1}$ |
| CE in the range of 30–400° C.: | $1.88 * 10^{-6}$ degree Celsius$^{-1}$ |
| CE in the range of 30–600° C.: | $2.6 * 10^{-6}$ degree Celsius$^{-1}$ |
| CE in the range of 30–800° C.: | $3.2 * 10^{-6}$ degree Celsius$^{-1}$ |

EXAMPLE 4

Chemical Stability of Apatite/CZP1 in the Alkaline Range

A vitreous-crystalline material according to Example 1 was produced (Apatite/CZP1). Subsequently, the material was ground in a mortar until a particle size fraction of 315–400 μm was obtained.

The chemical stability of the granulated material obtained in this way was compared to those of a basic glass ($Ap40_{glass}$) and a glass ceramic made from said basic glass and based on apatite and wollastonite ($Ap40_{cryst.}$) [i.e. with a chemical composition corresponding to (% by weight): 44.3 $SiO_2$; 11.3 $P_2O_5$; 31.9 CaO; 4.6 $Na_2O$; 0.19 $K_2O$; 2.82 MgO and 4.99 $CaF_2$].

First, the specific surface areas according to BET were determined using krypton as measuring gas. The following results were obtained:

| | |
|---|---|
| Apatite/CZP1: | 0.364 m$^2$/g |
| $Ap40_{glass}$: | 0.018 m$^2$/g |
| $Ap40_{cryst.}$: | 0.055 m$^2$/g. |

It can be seen that the vitreous-crystalline material used in the adhesive according to the invention has a certain open porosity compared to the basic glass and the glass ceramic made therefrom. These differences were taken into account in the solubility tests by adjusting the ratio of surface (sample) to volume of solvent (TRIS HCl buffer solution) to a constant value of 5 cm$^{-1}$.

The solvent used was a 0.2M TRIS HCl buffer solution, pH=7.4, at 37° C. The samples were stored therein for 120 hours at a temperature of 37° C. Then the samples' total solubility was determined by determining the individual ions (Ca, P, Zr) in the solution by means of an ICP measurement. The following results were obtained:

| | |
|---|---|
| Apatite/CZP1: | 4.1–5.1 mg/l |
| $Ap40_{glass}$: | 318–320 mg/l |
| $Ap40_{cryst.}$: | 75.2–82.0 mg/l. |

The above values impressively demonstrate the high chemical stability of the novel material used in the adhesive according to the invention under simulated physiological conditions, which is a known method for determining long-term stability in vitro.

EXAMPLE 5

Chemical Stability of Apatite/CZP1 in the Acid Range

The same procedure as in Example 4 was carried out, except that a 0.2M TRIS HCl buffer solution having a pH value of 6.0 and a temperature of 37° C. was used for measuring. In this way, an infection during the wound healing process or at a later stage causing the pH value to fall from the physiological value of 7.4 down into the acid range can be simulated.

The following total solubility values (Ca, P, Zr) were determined by means of ICP:

| | |
|---|---|
| Apatite/CZP1: | 16–19 mg/l |
| $Ap40_{glass}$: | 505–518 mg/l |
| $Ap40_{cryst.}$: | 117–125 mg/l. |

The above values impressively demonstrate the high chemical stability of the material used for the invention under simulated conditions corresponding to those during an inflammation reaction. According to the test results, the absolute solubility values of the material according to the invention increase to a much smaller extent than those of the basic glass and the glass ceramic based on apatite/wollastonite which rise quite dramatically.

EXAMPLES 6 to 8

In order to determine the tensile strength, an adhesive consisting of 30% polymer preparation, combined with a mixture of 60% by volume ethanol and 40% by volume ethyl acetoacetate as well as 35% by weight powder, was used to fix caps of In-Ceram (Vita Zahnfabrik), Galvanogold (Wieland Edelmetalle) and Express 2 (Ivoclar) to 4 mm high truncated cones of titanium with an upper diameter of 4.5 mm. The powder was made up of ZnO, $TiO_2$ and a vitreous-crystalline material according to Example 1. The samples were stored in water for 24 hours at 37° C. and subsequently their tensile strength was determined by pulling them apart at a rate of 1 mm/min using a Zwick all-purpose testing machine.

| Cap | Example 6<br>Empress 2 | Example 7<br>Galvanogold | Example 8<br>In-Ceram |
|---|---|---|---|
| Tensile strength after storage in water for 24 hours at 37°  | 35 N | 131 N | 129 N |
| After storage in water for 10 weeks | | 77 N | 78 N |

Compared to the known Havard Cement (zinc phosphate cement) whose tensile strength ranges between 300 and 600N, the tensile strengths of a material such as Empress 2 in connection with titanium are lower by approx. one order of magnitude and therefore well suitable for a temporary fixing.

Now that the invention has been described:
What is claimed is:

1. A method for the production of a temporary adhesive for metal-metal and metal-ceramic bonds comprising the steps of
    mixing 15 to 50% by weight, relative to the total weight of the adhesive, of a monomer-free polymethylmethacrylate (PMMA) whose average molar mass ranges between 3,000 and 200,000 daltons and whose acid value ranges between 10 and 350 mg KOH per g polymer with a biocompatible, organic solvent or solvent mixture for the PMMA, and
    adding 0.05 to 80% by weight, relative to the total weight of the adhesive, of a bioactive vitreous-crystalline material with a particle size ranging between 0.05 and 20 μm to the mixture, which material comprises 15–45% by weight CaO, 40–45% by weight $P_2O_5$, 10–40% by weight $ZrO_2$ and 0.7–3.5% by weight fluoride, relative to the total weight of the vitreous-crystalline material, and comprises apatite and calcium zirconium phosphate as main crystal phases and a glass phase as an auxiliary component, said main crystal phases of the vitreous-crystalline material jointly making up at least 35% by weight and said auxiliary components making up 5 to 15% by weight, while stirring and at a temperature ranging between 10 and 50° C. until a flowable mixture is obtained whose open processing dine ranges between 1 and 20 minutes.

2. The method according to claim 1, wherein a polymethyl-methacrylate is used in an amount ranging between 30 and 35% by weight.

3. The method according to claim 1, wherein the biocompatible solvent used is ethyl acetoacetate or a mixture of ethyl acetoacetate with ethanol, wherein the ethanol contains water up to an amount of 4% by volume.

4. The method according to claim 1, wherein another long-term stable or a totally or partially resorbable bioceramic is added to the vitreous-crystalline material 5. The method according to claim 4, wherein the bioceramic material used is a resorbable material comprising crystalline phases of $Ca_2KNa(PO_4)_2$ or a long-term stable glass ceramic based on apatite/wollastonite.

6. The method according to claim 1, wherein the vitreous-crystalline material used is a material comprising 23–39% by weight CaO, 40–45% by weight $P_2O_5$, 20–35% by weight $ZrO_2$ and 1–3% by weight fluoride.

7. The method according to claim 1, wherein the vitreous-crystalline material used is a material further comprising 0.1 to 6% by weight $Na_2O$ and additionally containing a sodium zirconium phosphate phase as an auxiliary component.

8. The method according to claim 1, wherein the vitreous-crystalline material used is a material having one or several of the following parameters:
    a total solubility ranging between 4 and 5.5 mg/l if the test is carried out in 0.2M TRIS HCl buffer solution at pH=7.4, T=37° C., using a particle size fraction of 315–400 μm, the duration of the test being 120 hours and the ratio of sample surface to volume of solvent being 5 $cm^{-1}$,
    a thermal coefficient of expansion ranging between 1.4 and $6*10^{-6}$ $degree^{-1}$ between 27° C. and 800° C.,
    stability in the pH range between 7.0 and 7.5.

9. The method according to claim 1, wherein a medicine is added to the starting components or mixtures thereof.

10. The method according to claim 1, wherein $TiO_2$ is added in an amount ranging between 0.1 and 10% by weight.

11. The method according to claim 1, further comprising, adding 3 to 30% by weight of a biocompatible powder containing zinc.

12. The method according to claim 1, wherein $CaZr_4(PO_4)_6$ or $CaTi_4(PO_4)_6$ or mixtures thereof or mixed crystals therefrom is/are added in an amount ranging up to 30% by weight in order to obtain an X-ray dense adhesive.

13. The method according to claim 1, wherein the viscosity of the adhesive is adjusted via the amount of the components making up the mixture and/or the molecular weight of the PMMA.

14. An adhesive kit based on polymethylmethacrylate comprising the following components provided separate of one another:
    a) 15 to 50% by weight, relative to the total weight of the adhesive, of a monomer-free polymethylmethacrylate (PMMA) whose average molar mass ranges between 3,000 and 200,000 daltons and whose acid value ranges between 10 and 350 mg KOR per g polymer;
    b) 10 to 40% by weight, relative to the total weight of the adhesive, of a biocompatible organic solvent or solvent mixture for the PMMA;
    c) 0.05 to 80% by weight, relative to the total weight of the adhesive, of a bioactive, vitreous-crystalline material with a particle size ranging between 0.05 and 20 μm comprising 15–45% by weight CaO, 40–45% by weight $P_2O_5$, 10–40% by weight $ZrO_2$ and 0.7–3.5% by weight $CaF_2$, relative to the total weight of the vitreous-crystalline material, and comprising apatite and calcium zirconium phosphate as main crystal phases and a glass phase as an auxiliary component, said main crystal phases of the vitreous-crystalline material jointly making up at least 35% by weight and said auxiliary components making up 5 to 15% by weight.

15. The adhesive kit according to claim 14, further comprising a component selected from the group consisting of $TiO_2$, an X-ray contrast medium, a resorbable bioceramic material comprising crystalline phases of $Ca_2KNa(PO_4)_2$, a long-term stable glass ceramic based on apatite/wollastonite and mixtures thereof.

16. The adhesive kit according to claim 14, further comprising 3 to 30% by weight of a biocompatible powder containing zinc.

17. The adhesive kit according to claim 14, wherein the biocompatible solvent is ethyl acetoacetate or a mixture of ethyl acetoacetate with ethanol, wherein the ethanol may contain water up to an amount of 4% by volume.

18. The method according to claim 3, wherein the biocompatible solvent used is ethyl acetoacetate.

19. The method according to claim 10, wherein the $TiO_2$ added comprises $TiO_2$ in the rutile form.

20. The method according to claim 11, wherein the biocompatible powder containing zinc contains zinc oxide or a zinc soap.

* * * * *